United States Patent [19]
Yoshigi et al.

[11] Patent Number: 5,863,784
[45] Date of Patent: Jan. 26, 1999

[54] RECOMBINANT β-AMYLASE

[75] Inventors: Naohiro Yoshigi; Hideo Maeba; Yukio Okada, all of Yaizu, Japan

[73] Assignee: Sapporo Breweries Ltd., Tokyo, Japan

[21] Appl. No.: 859,032

[22] Filed: May 20, 1997

Related U.S. Application Data

[62] Division of Ser. No. 531,601, Sep. 21, 1995, Pat. No. 5,688,684.

[30] Foreign Application Priority Data

Sep. 28, 1994 [JP] Japan .................................. 6-233086

[51] Int. Cl.$^6$ .............................. C12N 9/24; C12N 15/00; C12P 19/22; C08B 30/04
[52] U.S. Cl. ........................ 435/200; 435/95; 435/172.1; 435/275
[58] Field of Search .......................... 435/200, 95, 172.1, 435/275

[56] References Cited

U.S. PATENT DOCUMENTS

| | | | |
|---|---|---|---|
| 5,188,956 | 2/1993 | Nanmori et al | 435/200 |
| 5,273,762 | 12/1993 | Ahvenainen et al. | 426/11 |
| 5,312,739 | 5/1994 | Shaw | 435/95 |
| 5,726,057 | 3/1998 | Yoshigi et al. | 435/320.1 |

OTHER PUBLICATIONS

Oyo Toshitsu kagaku, vol. 41, No. 2, pp. 261–271, 1994, Naohiro Yoshigi et al., "Structure of Barley B–amylase and Expression in Escherichia Coli of cDNA".

Eur. J. Biochem., vol. 169, pp. 517–525, 1987, Martin Kreis et al., "Primary Structure and Differential Expression of B–amylase in Normal and Mutant Barleys".

Biosci. Biotech. Biochem, vol. 58, No. 6, pp. 1080–1086, 1994, Naohiro Yoshigi et al., "Expression in Escherichia Coli of cDNA Encoding Barley B–amylase and Properties of Recombinant B–amylase".

J. Biochem., vol. 115, pp. 47–51, 1994, Naohiro Yoshigi et al., "PCR Cloning and Sequencing of the B–amylase cDNA from Barley".

J. Biochem., vol. 118, pp. 562–567, 1995, Naohiro Yoshigi et al., "Construction of a Plasmid Used for the Expression of a Sevenfold–Mutant Barley B–amylase with Increased Thermostability in Escherichia Coli and Properties of the Sevenfold–Mutant B–amylase".

*Primary Examiner*—Robert A. Wax
*Assistant Examiner*—Lisa J. Hobbs
*Attorney, Agent, or Firm*—Oblon, Spivak, McClelland, Maier & Neustadt, P.C.

[57] ABSTRACT

A recombinant β-amylase which is superior to the original recombinant β-amylase in thermostability has been obtained by a site-directed mutagenesis with the recombinant β-amylase gene coding 531 amino acid residues. Substitutions were $MET_{181}$ of said enzyme with Leu, $Ser_{291}$ with Ala, $Ile_{293}$ with Val, $Ser_{346}$ with Pro, $Ser_{347}$ with Pro, $Gln_{348}$, with Asp and $Ala_{372}$ with Ser.

6 Claims, 3 Drawing Sheets

RECOMBINANT β-AMYLASE

This is a Division of application Ser. No. 08/531,601 filed on Sep. 21, 1995, now U.S. Pat. No. 5,688,684.

BACKGROUND OF THE INVENTION

1. Field of the Invention

This invention relates to a β-amylase with an improved thermostability as well as an improved enzyme stability in the alkaline pH region, a gene coding the enzyme and an expression vector containing the gene.

2. Description of the Related Art

Barley β-Amylase

Barley β-amylase is a β-amylase (1,4-α-D-glucan maltohydrolase [EC 3.2.1.2]) obtained from barley seeds and is well known along with soybean β-amylase, as a useful enzyme for the industrial maltose production used for transfusional solutions and foodstuffs.

However, since barley is one of the principal agricultural products for the production of livestock feeds and beverages (such as beer and whisky), from the viewpoint of the global food situation in the future it is not advisable to consume the harvested barley as a source of β-amylase.

Therefore, the method for producing β-amylase in microorganisms using genetic engineering techniques has been given attention as an other source of this enzyme than the barley. If the efficient expression of the barley β-amylase gene in a microorganism is accomplished, the steady supply of inexpensive β-amylase will become possible, obviously contributing a great deal to the maltose production.

Gene of Barley β-Amylase

As to the barley β-amylase gene, the cDNA consisted of 1754 base pairs of cultivar Hiproly has been reported, and also the amino acid sequence consisted of 535 residues has been deduced (Eur. J. Biochem., 169, 517 (1987)). In addition, the cDNA consisted of 1775 base pairs of cultivar. Haruna Nijo has been reported, and also the amino acid sequence consisted of 535 residues has been established (J. Biochem., 115, 47 (1994)).

In studies on β-amylase of cultivar Haruna Nijo, the expression vector (pBETA92) was already constructed by inserting a DNA fragment, which was prepared by deleting 55 base pairs of a full-length cDNA from its 5'-terminus and linking a SmaI linker, into the SmaI site of plasmid pKK223-3 (Pharmacia Biotech). Also the production of recombinant β-amylase has been accomplished by transforming *Escherichia coli* JM109 (Toyobo) with said expression vector and expressing the recombinant β-amylase gene therein. Furthermore, it was reported that the recombinant β-amylase comprising 531 amino acids showed almost the same properties as barley β-amylase (JP Hei6-58119; JP Hei6-303988).

However, a production of recombinant β-amylase in microorganisms which shows almost the same properties as those of β-amylase from barley seeds is not sufficient for the purpose. It is because of the fact that, since soybean β-amylase is superior a little more to barley β-amylase in the thermostability, soybean β-amylase is more widely used in practice. Therefore, in order to improve the utility value of the barley β-amylase, it is necessary to provide it at least with the similar function (thermostability) to that of soybean β-amylase.

As to the barley recombinant β-amylases with improved thermostability by protein engineering, it has been proved that double-mutant β-amylase wherein $Ser_{291}$ of the enzyme is replaced with Ala and $Ser_{346Ie}$ with Pro by site-directed mutagenesis is superior to the original recombinant β-amylase (JP Hei6-126151).

To further improve the utility value of recombinant β-amylase, it is necessary to construct β-amylase with a further improved thermostability by protein engineering.

SUMMARY OF THE INVENTION

The present invention aims to construct a gene of recombinant β-amylase with a further improved thermostability by site-directed mutagenesis, provide a recombinant vector containing the gene, get microorganisms transformed by the vector and eventually provide recombinant β-amylase with a further improved thermostability.

As a result of ardent studies to further improve the thermostability of β-amylase without changing the enzymatic function thereof, the inventors of the present invention have found that a sevenfold-mutant enzyme comprising the substitutions of $Met_{181}$ by Leu, $Ile_{293}$ by Val, $Ser_{347}$ by Pro, $Gln_{348}$, by Asp and $Ala_{372}$ by Ser in addition to those of $Ser_{291}$ by Ala and $Ser_{346}$ by Pro (JP Hei6-126151) was much superior to the double-mutant enzyme in thermostability accomplishing the present invention.

That is, the recombinant β-amylase according to the present invention is that comprising the amino acid sequence denoted by SEQ ID NO: 1.

β-Amylase according to the present invention is a recombinant β-amylase which acts on polysaccharides having α-1,4-glucoside linkages such as soluble starch, amylose and amylopectin in addition to maltooligosaccharides with a degree of polymerization higher than 3 liberating successively a β-maltose unit from the non-reducing ends thereof, shows more than 80% of the maximum enzymatic activity at pH 3.5~7.0 (37° C.), retains more than 80% remaining activity after the treatment for 1 h at pH 3.5~12.5 (37° C.), shows the maximum activity toward soluble starch at 65° C. and 87% of the maximum activity at 70° C. (pH 7.0), and is stable after treatment for 30 min till up to 62.5° C. in the absence of a substrate at pH 7.0.

Furthermore, a gene related to the present invention is the gene coding recombinant β-amylase comprising the amino acid sequence of SEQ ID NO: 1.

Gene according to the present invention is the gene coding recombinant β-amylase of claim 1 having the nucleotide sequence of SEQ ID NO: 2.

Expression vector according to the present invention is the expression vector for β-amylase comprising any one of the genes described above. An Expression vector of this sort is exemplified by that having the nucleotide sequence of SEQ ID NO: 3.

Host cells according to the present invention are those containing the expression vectors.

In the following, there will be described the practical method for preparing recombinant β-amylase according to the present invention, a gene coding the enzyme and an expression vector containing the gene.

1. Base substitution of β-amylase expression vector pBETA92 by site-directed mutagenesis The base substitution at the specific site of the gene sequence of β-amylase expression vector pBETA92 can be achieved by site-directed mutagenesis (Anal. Biochem., 200, 81 (1992).

2. Transformation host microorganism with β-amylase expression vector

Any microorganisms can be used as the host cell so far as the expression vector for β-amylase with the improved thermostability can proliferate stably and autonomously therein.

As to the method to transform the host microorganism with the expression vector for recombinant β-amylase, any published method, for example, the competent cell method (J. Mol. Biol., 58, 159 (1970)) may be used in the case where the host microorganism is *Escherichia coli*.

3. Confirmation of DNA sequence

DNA sequence can be performed by the chemical modification method according to Maxam-Gilbert (Methods in Enzymology, 65, 499 (1980)) or the dideoxynucleotide chain termination method (Gene, 19, 269 (1982)) or the like.

Furthermore, the amino acid sequence of β-amylase according to the present invention can be deduced from the DNA sequence.

4. Production and purification of recombinant β-amylase

After growing the host microorganism harboring the β-amylase expression vector for a certain period, the pure preparation of recombinant β-amylase can be obtained by cell lysis, if necessary, followed by a combination of ammonium sulfate fractionation and various chromatographies such as gel filtration or ion exchange.

β-Amylase activity may be assayed using 2.4-dichlorophenyl β-maltopentaoside (Ono Pharmaceutical) as the substrate. In this case, one unit of enzyme is defined as the amount of enzyme which produces 1 μmol of dichlorophenol per min at 37° C.

5. Estimation of thermostability

Aliquot of enzyme preparation (30 μl each) in 1.5-ml Eppendorf tubes was incubated at 50°~72.5° C. (with 2.5° C.-intervals) in a water bath for 30 min. The remaining activity was assayed using 20 μl aliquot withdrawn from the tube. The remaining activity versus temperature curves were used to determine the temperature curves of enzyme relative at which 50% of the initial activity was lost during 30-min heating period and half-inactivation temperature values provided a parameter for the ranking of thermal stabilities of the enzyme.

Soybean β-amylase used as a control is one purchased from Amano Pharmaceutical (trade name, Biozyme M-5). The enzyme preparation was diluted using a solution of 50 mM Good's buffer (pH 7.0)/1% bovine serum albumin.

Studies of effects of temperature and pH on β-amylase activity were done by reacting the enzyme with soluble starch at pH 7.0. The amount of the reducing sugar produced was measured by the dinitrosalicylic acid method (Denpun Kagaku Handbook, Asakurashoten, p. 188–189 (1977)), and 1 unit of the enzyme was defined as the amount which liberates 1 μmol of maltose per min.

6. Determination of optimum pH

The reaction mixture, 0.4 ml of 1% soluble starch solution, 0.2 ml of various buffers (described below) and 0.2 ml of enzyme preparation, was incubated at 37° C. The amount of reducing sugars produced was measured by the dinitrosalicylic acid method, and results were expressed as the value relative to the maximum activity (100%). As a result of measuring the optimum pH in this manner, the optimum pH at which the enzyme shows more than 80% of the maximum activity was found to be in the range of 3.5~7.0.

Buffers used were as follows:

| | |
|---|---|
| pH 2.5~3.0 | Citrate buffer |
| pH 3.5~5.5 | Acetate buffer |
| pH 6.0~8.0 | Good's buffer |

-continued

| | |
|---|---|
| pH 8.5 | Tris-maleate buffer |
| pH 9.0~11.0 | Glycine buffer |

7. Determination of pH stability

To the enzyme preparation (50 μl) was added 100 mM various buffers (50 μl) and the mixture was incubated at 37° C. for 1 h. Then 0.9 ml of 500 mM Good's buffer (pH 7.0)/1% bovine serum albumin solution was added. To 0.4 ml aliquot withdrawn was added 0.4 ml of 1% soluble starch solution (pH 7.0), and the mixture was incubated at 37° C. and the remaining enzymatic activity was measured. As a result of measuring pH stability in this manner, the pH range where more than 80% of the original activity was stably retained was found to be 3.5~12.5.

Buffers used were as follows:

| | |
|---|---|
| pH 3.0 | Citrate buffer |
| pH 3.5~5.5 | Acetate buffer |
| pH 6.0~8.0 | Good's buffer |
| pH 8.5 | Tris-maleate buffer |
| pH 9.0~11.5 | Glycine buffer |
| pH 12.0~13.0 | KCl—NaOH buffer |

DESCRIPTION OF THE PREFERRED EMBODIMENT

Figure 1:
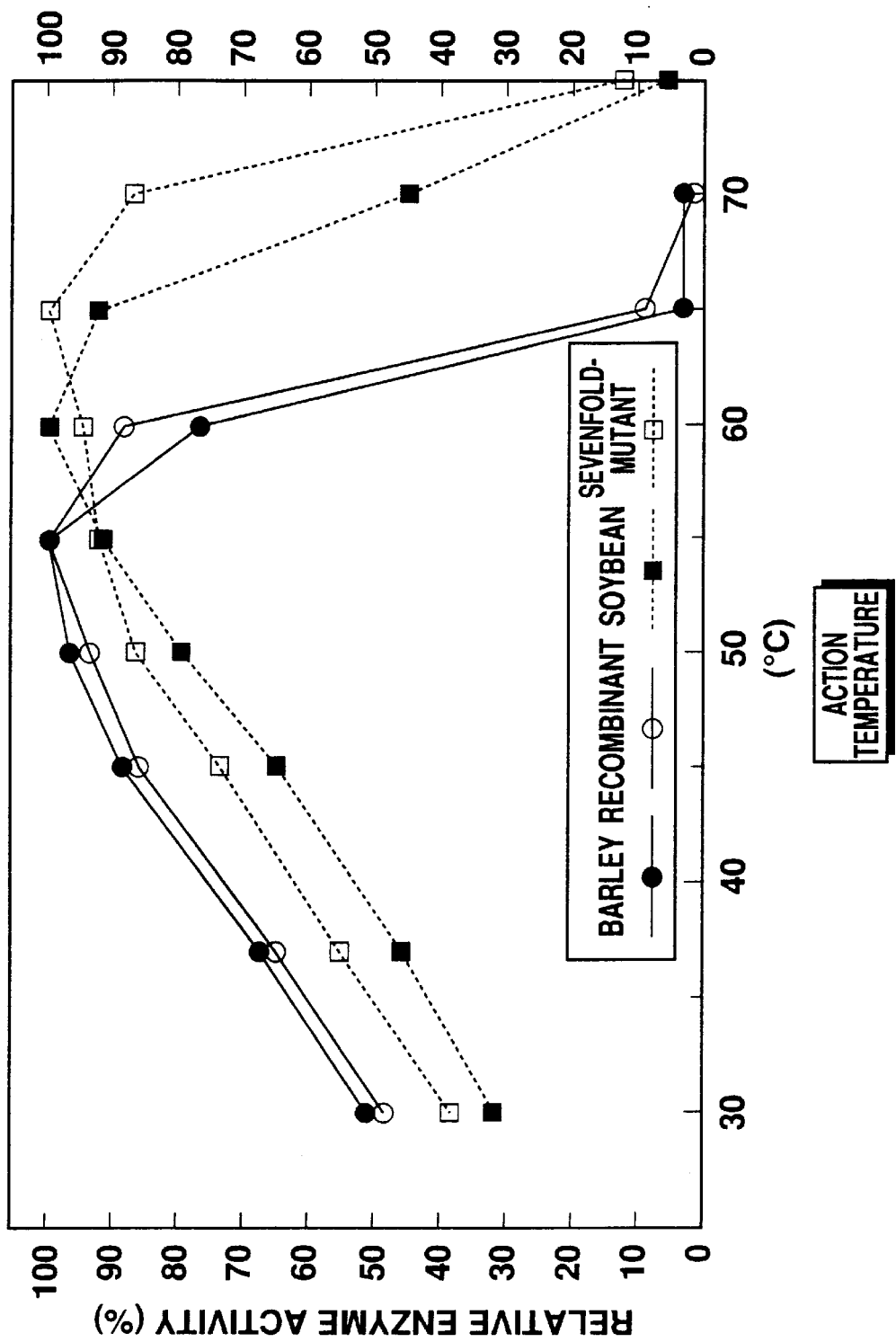
FIG. 1 is a drawing showing the optimum temperature of each preparation. In the figure, (□. . . □) indicates sevenfold-mutant β-amylase according to the present invention, (●-●) barley β-amylase, (○-○) original recombinant β-amylase and (■. . . ■) soybean β-amylase.

The invention will now be described in further detail with reference to specific examples, however, it is understood that the scope of the present invention is not to be construed as being limited to them in any way.

EXAMPLE 1

Base substitution of the recombinant β-amylase expression vector by the site-directed mutagenesis The site-directed mutagenesis was done using a Transfer Site-directed Mutagenesis kit (Clontech Laboratories).

Using the following four mutagenesis primers
5'-AGCTGGAGAGTTGAGGTACCC-3' (for $Met_{181}$ to Leu; SEQ ID NO: 4),
5'-AATCAAGATCGCTGGCGTTCACTGGTG-3' (for $Ser_{291}$ to Ala and $Ile_{293}$ to Val; SEQ ID NO: 5),
5'-TTCGGAGCAACCCCCGGACGCGATGAGCGCA-3' (for $Ser_{346}$ to Pro, $Ser_{347}$ to Pro and $Gln_{348}$ to Asp; SEQ ID NO: 6) and
5'-CCTAAATGTGTCATGCGAAAA-3' (for $Ala_{372}$ to Ser; SEQ ID NO: 7)

and the selection primer 5'-GGTTGAGTATTCACCAGTC-3' (SEQ ID NO: 8), the site-directed mutagenesis was done according to the manual provided with the kit to obtain the recombinant β-amylase (sevenfold-mutant β-amylase) expression vector (pBETA92/sevenfold-mutant) as shown in SEQ ID NO: 3.

EXAMPLE 2
Determination of DNA sequence

DNA sequence confirmed that, as shown in SEQ ID NO: 2 in the sequence list, $A_{541}$ was substituted with T, $T_{871}$ with G, $A_{877}$ with G, $AG_{1036-1037}$ with CC, $T_{1039}$ with C, $C_{1042}$ with G, $G_{1044}$ with C and $G_{1114}$ with T. Consequently, it was confirmed that the expression vector pBETA92/sevenfold-mutant is coding the recombinant β-amylase as shown in SEQ ID NO: 1 of the sequence list.

EXAMPLE 3
Production and purification of recombinant β-amylase

*Escherichia coli* JM109 harboring the expression vector pBETA92/sevenfold-mutant was grown in a liquid medium (containing 1% Tryptone, 0.5% yeast extract, 1% NaCl, 0.005% Ampicillin Na and 0.1 mM isopropyl β-D-thiogalactopyranoside in 400 ml of water, pH 7.0) at 37° C. for 24 h. After centrifugation to remove the culture medium, packed cells were suspended in a lysozyme solution (0.025% lysozyme, 20 mM Tris-HCl and 30 mM NaCl, pH 7.5) for 30 min on ice, and disrupted by sonication (50 W, 30 sec) followed by centrifugation.

To the above crude extract was added solid ammonium sulfate to 30% saturation. After the precipitate was removed by centrifugation, the supernatant was loaded onto a Butyl Toyopearl 650S (Toso) column (2.5×18.5 cm). The active fractions which were eluted with 50 mM acetate buffer (pH 5.5) were collected and dialyzed against 15 mM Tris-HCl (pH 8.0). The dialyzed solution was centrifuged to remove insoluble materials and then loaded onto a DEAE-Toyopearl 650S (Toso) column (2.5×18.5 cm). The active fractions which were eluted with 15 mM Tris-HCl (pH 8.0)/50 mM NaCl were collected, and added solid ammonium sulfate to 70% saturation. The precipitate formed were collected by centrifugation, dissolved in 50 mM acetate buffer (pH 5.5) and then dialyzed against the same buffer. Then the dialyzed solution was loaded onto a Toyopearl HW-50S (Toso) column (1.5×48.5 cm). The active fractions which were eluted with 50 mM acetate buffer (pH 5.5) were combined as the purified preparation of the recombinant β-amylase. On SDS-polyacrylamide gel electrophoresis the purified preparation showed a single protein band at an apparent-molecular weight of 56,000 which migrated to almost the same position as the original recombinant β-amylase.

EXAMPLE 4
Enzymatic properties of sevenfold-mutant β-amylase

Comparison of the enzymatic properties of the sevenfold-mutant β-amylase with those of the original recombinant β-amylase revealed that both enzymes were almost similar except for the optimum temperature, thermostability and pH stability.

Results of studies on the optimum temperature are shown in FIG. 1. In contrast to the barley β-amylase and the original recombinant β-amylase which showed the maximum activity at 55° C. and almost no activity at 65°~70° C., the sevenfold-mutant β-amylase was found to show the maximum activity at 65° C. and a significant activity even at 70° C. It was also confirmed that the sevenfold-mutant β-amylase was significantly improved in thermostability as compared with the soybean β-amylase which showed the maximum activity at 60° C.

Figure 2:
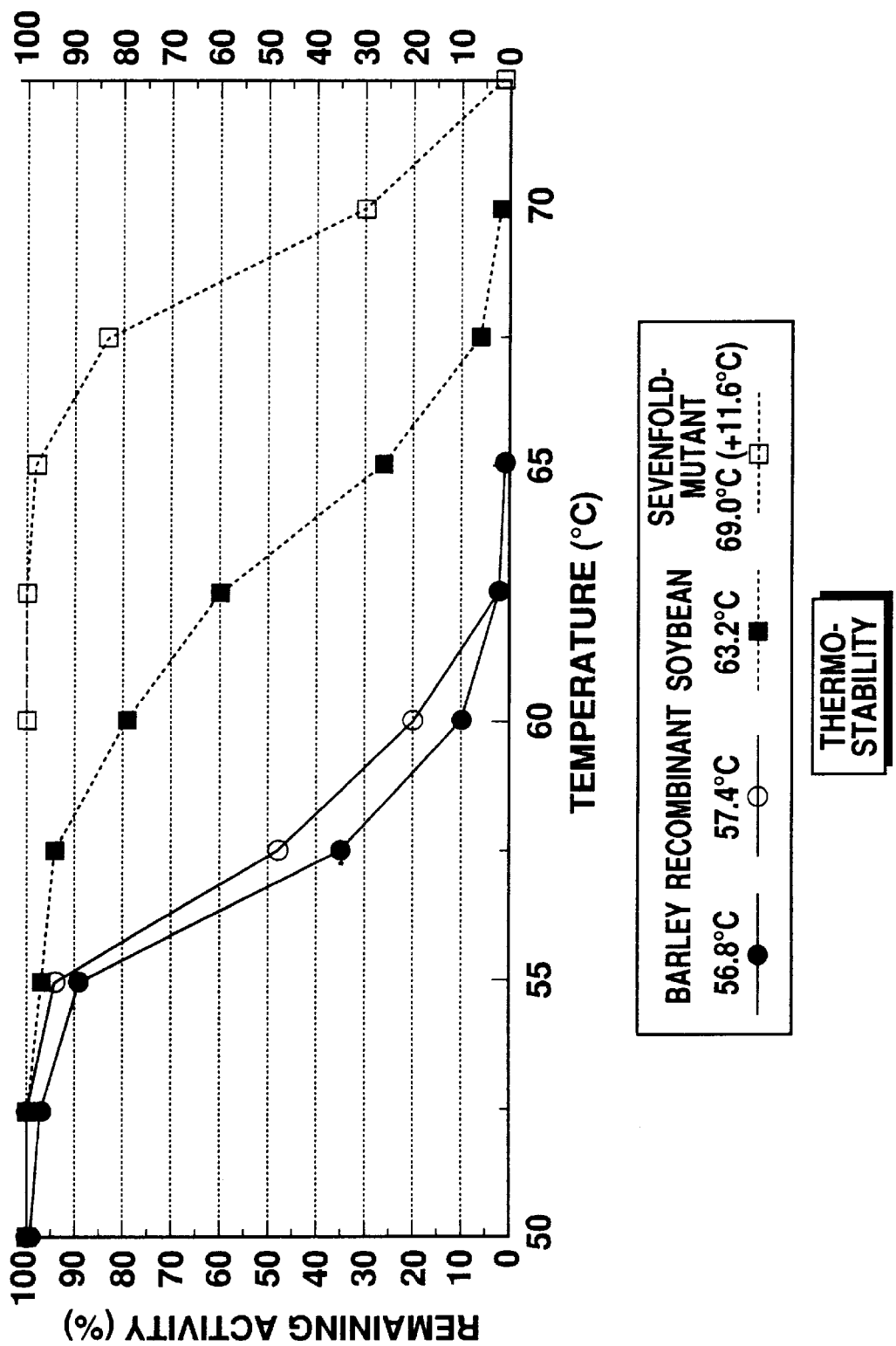
FIG. 2 is a drawing showing the thermostability of each preparation. In the figure, (□. . . □) indicates sevenfold-mutant β-amylase according to the present invention, (●-●) barley β-amylase, (○-○) original recombinant β-amylase and (■. . . ■) soybean β-amylase.

From heat-inactivation curves shown in FIG. 2, temperatures at which 50% of the initial activity was lost during a 30 min heating time were found as follows:

| | | |
|---|---|---|
| barley β-amylase | → | 56.8° C. |
| original recombinant β-amylase | → | 57.4° C. |
| sevenfold-mutant β-amylase | → | 69.0° C. |
| soybean β-amylase | → | 63.2° C. |

The results indicate that the thermostability of the sevenfold-β-amylase was improved by 11.6° C. than that of the original recombinant β-amylase, and furthermore by 5.8° C. than that of the soybean β-amylase.

A great deal improvement of the sevenfold-mutant β-amylase in the thermostability was confirmed by the fact that, while the original recombinant β-amylase was almost completely inactivated by treatment at 62.5° C. for 30 min, the sevenfold-mutant β-amylase was not inactivated at all by the same treatment.

Figure 3:
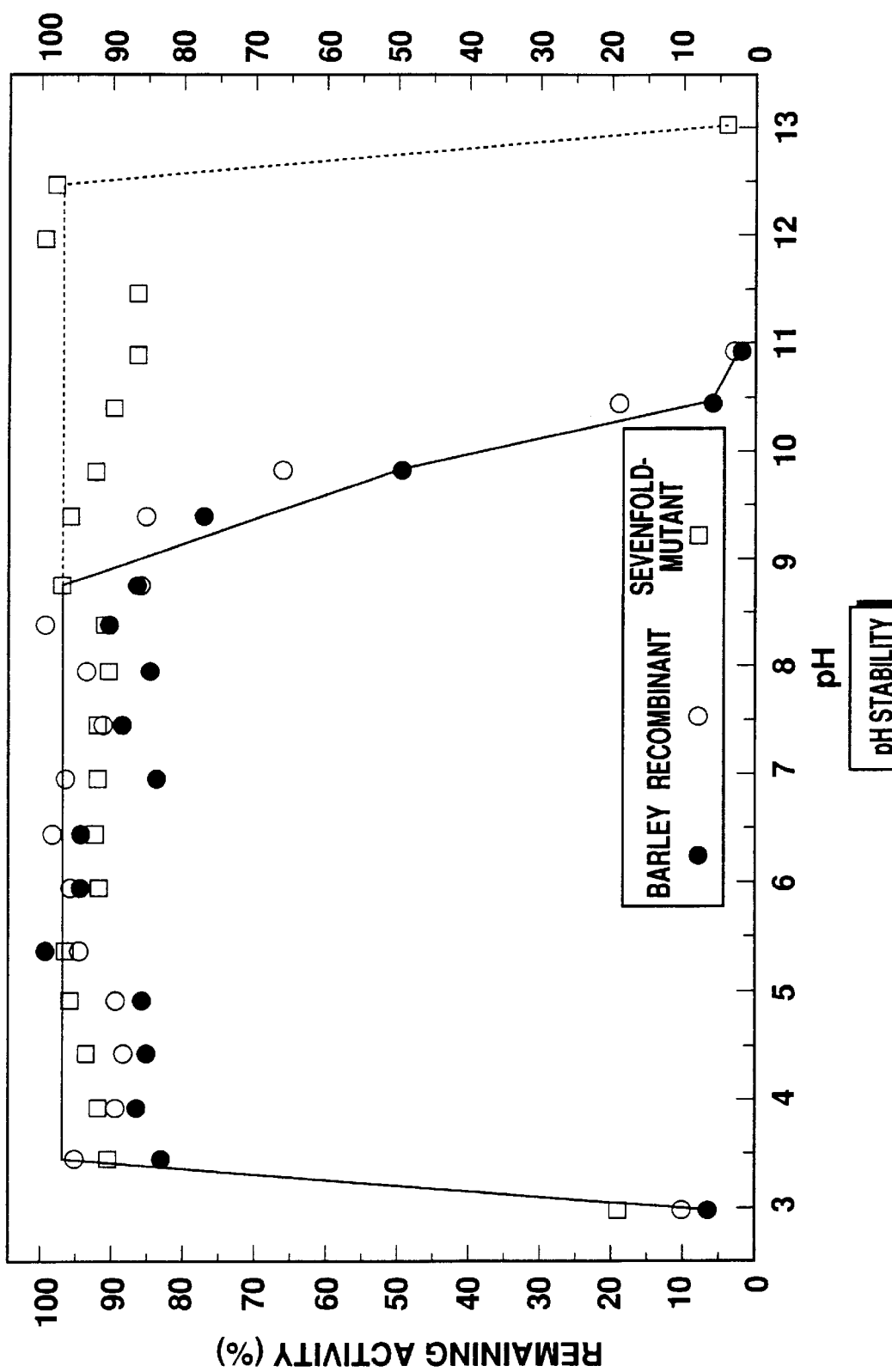
FIG. 3 is a drawing showing the pH stability of each preparation. In the figure, (□. . . □) indicates sevenfold-mutant β-amylase according to the present invention, (●-●) barley β-amylase and (○-○) original recombinant β-amylase.

As to the pH stability, as shown in FIG. 3, while the barley β-amylase and the original recombinant β-amylase were stable in the pH range of 3.5~9.5, the sevenfold-mutant β-amylase was stable in the pH range of 3.5~12.5, indicating a significant improvement in the stability of the latter β-amylase in the alkaline pH range.

The present invention has made it possible to produce a recombinant β-amylase with improved thermostability as well as improved enzyme stability in the alkaline pH range.

What is claimed is:

1. A recombinant β-amylase having an amino acid sequence denoted by SEQ ID NO: 1.

2. A recombinant β-amylase having the following enzymatic properties:
   (1) an ability to liberate successive β-maltose units from the non-reducing ends of α-1,4-glucans;
   (2) an ability to hydrolyze polysaccharides having α-1,4-glucoside linkages and a degree of polymerization higher than 3;
   (3) retains enzymatic activity at 37° C. from pH 3.5 to 7.0;
   (4) retains enzymatic activity after treatment at 37° C. for 1 hour at pH 3.5 to 12.5;
   (5) an optimum temperature of 65° C. at pH 7.0 for enzymatic activity towards soluble starch as a substrate; and
   (6) remains stable in absence of a substrate after treatment for 30 minutes at pH 7.0 at a temperature from 50° to 62.5° C.

3. The recombinant (β-amylase of claim 2, which retains, at 70° C. and pH 7.0, 87% of the enzymatic activity towards soluble starch as the substrate, wherein 100% of the enzymatic activity towards soluble starch is defined as the enzymatic activity towards soluble starch at 65° C. and pH 7.0.

4. The recombinant β-amylase of claim 2, which has an apparent molecular weight of 56,000 as measured by SDS-polyacrylamide gel electrophoresis.

5. The recombinant β-amylase of claim 2, wherein said polysaccharides having α-1,4-glucoside linkages are selected from the group consisting of soluble starch, amylose and amylopectin.

6. The recombinant β-amylase of claim 2, wherein said polysaccharides having α-1,4-glucoside linkages are maltooligosaccharides.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 531 amino acids
        ( B ) TYPE: amino acid
        ( C ) STRANDEDNESS: single
        ( D ) TOPOLOGY: linear ( i i ) MOLECULE TYPE: protein (xi) SEQUENCE DESCRIPTION: SEQ ID NO:1:

| | | | | | | | | | | | | | | |
|---|---|---|---|---|---|---|---|---|---|---|---|---|---|---|
| Met 1 | Lys | Gly | Asn | Tyr 5 | Val | Gln | Val | Tyr | Val 10 | Met | Leu | Pro | Leu | Asp 15 | Ala |
| Val | Ser | Val | Asn 20 | Asn | Arg | Phe | Glu | Lys 25 | Gly | Asp | Glu | Leu | Arg 30 | Ala | Gln |
| Leu | Arg | Lys 35 | Leu | Val | Glu | Ala | Gly 40 | Val | Asp | Gly | Val | Met 45 | Val | Asp | Val |
| Trp | Trp 50 | Gly | Leu | Val | Glu | Gly 55 | Lys | Gly | Pro | Lys | Ala 60 | Tyr | Asp | Trp | Ser |
| Ala 65 | Tyr | Lys | Gln | Leu | Phe 70 | Glu | Leu | Val | Gln | Lys 75 | Ala | Gly | Leu | Lys | Leu 80 |
| Gln | Ala | Ile | Met | Ser 85 | Phe | His | Gln | Cys | Gly 90 | Gly | Asn | Val | Gly | Asp 95 | Ala |
| Val | Asn | Ile | Pro 100 | Ile | Pro | Gln | Trp | Val 105 | Arg | Asp | Val | Gly | Thr 110 | Arg | Asp |
| Pro | Asp | Ile 115 | Phe | Tyr | Thr | Asp | Gly 120 | His | Gly | Thr | Arg | Asn 125 | Ile | Glu | Tyr |
| Leu | Thr 130 | Leu | Gly | Val | Asp | Asn 135 | Gln | Pro | Leu | Phe | His 140 | Gly | Arg | Ser | Ala |
| Val 145 | Gln | Met | Tyr | Ala | Asp 150 | Tyr | Met | Thr | Ser | Phe 155 | Arg | Glu | Asn | Met | Lys 160 |
| Asp | Phe | Leu | Asp | Ala 165 | Gly | Val | Ile | Val | Asp 170 | Ile | Glu | Val | Gly | Leu 175 | Gly |
| Pro | Ala | Gly | Glu 180 | Leu | Arg | Tyr | Pro | Ser 185 | Tyr | Pro | Gln | Ser | His 190 | Gly | Trp |
| Ser | Phe | Pro 195 | Gly | Ile | Gly | Glu | Phe 200 | Ile | Cys | Tyr | Asp | Lys 205 | Tyr | Leu | Gln |
| Ala | Asp 210 | Phe | Lys | Ala | Ala | Ala 215 | Ala | Val | Gly | His | Pro 220 | Glu | Trp | Glu |
| Phe 225 | Pro | Asn | Asp | Ala | Gly 230 | Gln | Tyr | Asn | Asp | Thr 235 | Pro | Glu | Arg | Thr | Gln 240 |
| Phe | Phe | Arg | Asp | Asn 245 | Gly | Thr | Tyr | Leu | Ser 250 | Glu | Lys | Gly | Arg | Phe 255 | Phe |
| Leu | Ala | Trp | Tyr 260 | Ser | Asn | Asn | Leu | Ile 265 | Lys | His | Gly | Asp | Arg 270 | Ile | Leu |
| Asp | Glu | Ala 275 | Asn | Lys | Val | Phe | Leu 280 | Gly | Tyr | Lys | Val | Gln 285 | Leu | Ala | Ile |
| Lys | Ile 290 | Ala | Gly | Val | His | Trp 295 | Trp | Tyr | Lys | Val | Pro 300 | Ser | His | Ala | Ala |
| Glu 305 | Leu | Thr | Ala | Gly | Tyr 310 | Tyr | Asn | Leu | His | Asp 315 | Arg | Asp | Gly | Tyr | Arg 320 |
| Thr | Ile | Ala | Arg | Met 325 | Leu | Lys | Arg | His | Arg 330 | Ala | Ser | Ile | Asn | Phe 335 | Thr |
| Cys | Ala | Glu | Met 340 | Arg | Asp | Ser | Glu | Gln 345 | Pro | Pro | Asp | Ala | Met 350 | Ser | Ala |
| Pro | Glu | Glu 355 | Leu | Val | Gln | Gln | Val 360 | Leu | Ser | Ala | Gly | Trp 365 | Arg | Glu | Gly |
| Leu | Asn 370 | Val | Ser | Cys | Glu | Asn 375 | Ala | Leu | Pro | Arg | Tyr 380 | Asp | Pro | Thr | Ala |
| Tyr 385 | Asn | Thr | Ile | Leu | Arg 390 | Asn | Ala | Arg | Pro | His 395 | Gly | Ile | Asn | Gln | Ser 400 |
| Gly | Pro | Pro | Glu | His 405 | Lys | Leu | Phe | Gly | Phe 410 | Thr | Tyr | Leu | Arg | Leu 415 | Ser |

| Asn | Gln | Leu | Val<br>420 | Glu | Gly | Gln | Asn | Tyr<br>425 | Val | Asn | Phe | Lys | Thr<br>430 | Phe | Val |

| Asp | Arg | Met<br>435 | His | Ala | Asn | Leu | Pro<br>440 | Arg | Asp | Pro | Tyr | Val<br>445 | Asp | Pro | Met |

| Ala | Pro<br>450 | Leu | Pro | Arg | Ser | Gly<br>455 | Pro | Glu | Ile | Ser | Ile<br>460 | Glu | Met | Ile | Leu |

| Gln | Ala | Ala | Gln | Pro | Lys<br>470 | Leu | Gln | Pro | Phe | Pro<br>475 | Phe | Gln | Glu | His | Thr<br>480 |
| 465 | | | | | | | | | | | | | | | |

| Asp | Leu | Pro | Val | Gly<br>485 | Pro | Thr | Gly | Gly | Met<br>490 | Gly | Gly | Gln | Ala | Glu<br>495 | Gly |

| Pro | Thr | Cys | Gly<br>500 | Met | Gly | Gly | Gln | Val<br>505 | Lys | Gly | Pro | Thr | Gly<br>510 | Gly | Met |

| Gly | Gly | Gln<br>515 | Ala | Glu | Asp | Pro | Thr<br>520 | Ser | Gly | Met | Gly | Gly<br>525 | Glu | Leu | Pro |

| Ala | Thr | Met |
| | | 530 |

(2) INFORMATION FOR SEQ ID NO:2:

(i) SEQUENCE CHARACTERISTICS:
        (A) LENGTH: 1596 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

```
GTGAAAGGCA ACTATGTCCA AGTCTACGTC ATGCTCCCTC TGGACGCCGT GAGCGTGAAC      60
AACAGGTTCG AGAAGGGCGA CGAGCTGAGG GCGCAATTGA GGAAGCTGGT AGAGGCCGGT     120
GTGGATGGTG TCATGGTAGA CGTCTGGTGG GGCTTGGTGG AGGGCAAGGG CCCCAAGGCG     180
TATGACTGGT CCGCCTACAA GCAGTTGTTT GAGCTGGTGC AGAAGGCTGG GCTGAAGCTA     240
CAGGCCATCA TGTCGTTCCA CCAGTGTGGT GGCAACGTCG GCGACGCCGT CAACATCCCA     300
ATCCCACAGT GGGTGCGGGA CGTCGGCACG CGTGATCCCG ACATTTTCTA CACCGACGGT     360
CACGGGACTA GGAACATTGA GTACCTCACT CTTGGAGTTG ATAACCAGCC TCTCTTCCAT     420
GGAAGATCTG CCGTCCAGAT GTATGCCGAT TACATGACAA GCTTCAGGGA GAACATGAAA     480
GACTTCTTGG ATGCTGGTGT TATCGTCGAC ATTGAAGTGG ACTTGGCCC AGCTGGAGAG      540
TTGAGGTACC CATCATATCC TCAGAGCCAC GGATGGTCGT TCCCAGGCAT CGGAGAATTC     600
ATCTGCTATG ATAAATACCT ACAAGCAGAC TTCAAAGCAG CAGCAGCGGC GGTCGGCCAT     660
CCTGAGTGGG AATTTCCTAA CGATGCCGGA CAGTACAATG ACACTCCCGA GAGAACTCAA     720
TTCTTCAGGG ACAACGGGAC ATACCTAAGT GAGAAGGGGA GGTTTTTCCT TGCATGGTAC     780
TCCAACAATC TGATCAAGCA CGGTGACAGG ATCTTGGATG AAGCAAACAA GGTCTTCTTG     840
GGATACAAGG TGCAATTGGC AATCAAGATC GCTGGCGTTC ACTGGTGGTA CAAGGTTCCA     900
AGCCATGCAG CCGAGCTCAC AGCTGGGTAC TATAACTTAC ATGATAGAGA CGGCTACAGA     960
ACCATAGCAC GCATGCTCAA AAGGCACCGT GCTAGCATTA ACTTCACTTG CGCGGAGATG    1020
AGGGATTCGG AGCAACCCCC GGACGCGATG AGCGCACCAG AAGAACTAGT CCAACAGGTG    1080
TTGAGTGCTG GATGGAGAGA GGGCCTAAAT GTGTCATGCG AAAACGCGCT TCCACGATAT    1140
GATCCAACTG CTTACAACAC CATACTCAGG AATGCGAGGC CTCATGGAAT CAACCAGAGC    1200
GGCCCTCCTG AGCACAAGCT GTTTGGATTC ACCTACCTTC GGCTGTCGAA TCAGCTGGTG    1260
GAGGGACAAA ACTATGTCAA CTTCAAGACC TTTGTCGACA GAATGCATGC CAACCTGCCT    1320
```

| | | | | | |
|---|---|---|---|---|---|
| CGTGACCCAT | ATGTTGATCC | AATGGCGCCC | TTGCCAAGAT | CAGGGCCAGA | AATATCGATT 1380 |
| GAGATGATCC | TACAAGCAGC | ACAGCCAAAA | CTGCAGCCAT | TCCCCTTCCA | GGAGCACACC 1440 |
| GACCTGCCAG | TAGGCCCTAC | TGGTGGCATG | GGTGGGCAGG | CTGAAGGCCC | CACCTGTGGC 1500 |
| ATGGGTGGGC | AAGTTAAAGG | CCCTACTGGT | GGCATGGGTG | GCAGGCTGA | AGACCCTACT 1560 |
| AGTGGCATGG | GTGGGGAGCT | CCCTGCCACC | ATGTAA | | 1596 |

( 2 ) INFORMATION FOR SEQ ID NO:3:

( i ) SEQUENCE CHARACTERISTICS:
( A ) LENGTH: 6312 base pairs
( B ) TYPE: nucleic acid
( C ) STRANDEDNESS: double
( D ) TOPOLOGY: circular ( i i ) MOLECULE TYPE: DNA (genomic)

( x i ) SEQUENCE DESCRIPTION: SEQ ID NO:3:

| | | | | | |
|---|---|---|---|---|---|
| TTCCGGGATG | GAGGTGAACG | TGAAAGGCAA | CTATGTCCAA | GTCTACGTCA | TGCTCCCTCT 60 |
| GGACGCCGTG | AGCGTGAACA | ACAGGTTCGA | GAAGGGCGAC | GAGCTGAGGG | CGCAATTGAG 120 |
| GAAGCTGGTA | GAGGCCGGTG | TGGATGGTGT | CATGGTAGAC | GTCTGGTGGG | GCTTGGTGGA 180 |
| GGGCAAGGGC | CCCAAGGCGT | ATGACTGGTC | CGCCTACAAG | CAGTTGTTTG | AGCTGGTGCA 240 |
| GAAGGCTGGG | CTGAAGCTAC | AGGCCATCAT | GTCGTTCCAC | CAGTGTGGTG | GCAACGTCGG 300 |
| CGACGCCGTC | AACATCCCAA | TCCCACAGTG | GGTGCGGGAC | GTCGGCACGC | GTGATCCCGA 360 |
| CATTTTCTAC | ACCGACGGTC | ACGGGACTAG | GAACATTGAG | TACCTCACTC | TTGGAGTTGA 420 |
| TAACCAGCCT | CTCTTCCATG | GAAGATCTGC | CGTCCAGATG | TATGCCGATT | ACATGACAAG 480 |
| CTTCAGGGAG | AACATGAAAG | ACTTCTTGGA | TGCTGGTGTT | ATCGTCGACA | TTGAAGTGGG 540 |
| ACTTGGCCCA | GCTGGAGAGT | TGAGGTACCC | ATCATATCCT | CAGAGCCACG | GATGGTCGTT 600 |
| CCCAGGCATC | GGAGAATTCA | TCTGCTATGA | TAAATACCTA | CAAGCAGACT | TCAAAGCAGC 660 |
| AGCAGCGGCG | GTCGGCCATC | CTGAGTGGGA | ATTTCCTAAC | GATGCCGGAC | AGTACAATGA 720 |
| CACTCCCGAG | AGAACTCAAT | TCTTCAGGGA | CAACGGGACA | TACCTAAGTG | AGAAGGGGAG 780 |
| GTTTTTCCTT | GCATGGTACT | CCAACAATCT | GATCAAGCAC | GGTGACAGGA | TCTTGGATGA 840 |
| AGCAAACAAG | GTCTTCTTGG | GATACAAGGT | GCAATTGGCA | ATCAAGATCG | CTGGCGTTCA 900 |
| CTGGTGGTAC | AAGGTTCCAA | GCCATGCAGC | CGAGCTCACA | GCTGGGTACT | ATAACTTACA 960 |
| TGATAGAGAC | GGCTACAGAA | CCATAGCACG | CATGCTCAAA | AGGCACCGTG | CTAGCATTAA 1020 |
| CTTCACTTGC | GCGGAGATGA | GGGATTCGGA | GCAACCCCG | GACGCGATGA | GCGCACCAGA 1080 |
| AGAACTAGTC | CAACAGGTGT | TGAGTGCTGG | ATGGAGAGAG | GGCCTAAATG | TGTCATGCGA 1140 |
| AAACGCGCTT | CCACGATATG | ATCCAACTGC | TTACAACACC | ATACTCAGGA | ATGCGAGGCC 1200 |
| TCATGGAATC | AACCAGAGCG | GCCCTCCTGA | GCACAAGCTG | TTTGGATTCA | CCTACCTTCG 1260 |
| GCTGTCGAAT | CAGCTGGTGG | AGGGACAAAA | CTATGTCAAC | TTCAAGACCT | TGTCGACAG 1320 |
| AATGCATGCC | AACCTGCCTC | GTGACCCATA | TGTTGATCCA | ATGGCGCCCT | TGCCAAGATC 1380 |
| AGGGCCAGAA | ATATCGATTG | AGATGATCCT | ACAAGCAGCA | CAGCCAAAAC | TGCAGCCATT 1440 |
| CCCCTTCCAG | GAGCACACCG | ACCTGCCAGT | AGGCCCTACT | GGTGGCATGG | GTGGGCAGGC 1500 |
| TGAAGGCCCC | ACCTGTGGCA | TGGGTGGGCA | AGTTAAAGGC | CCTACTGGTG | GCATGGGTGG 1560 |
| GCAGGCTGAA | GACCCTACTA | GTGGCATGGG | TGGGGAGCTC | CCTGCCACCA | TGTAATGGAA 1620 |
| CCTTTATGAT | TTACTACCCT | TTATGTTGTG | TGTGAGTGTG | ACAGAGAAAC | CTTTCTCTGC 1680 |

-continued

| | | | | | | |
|---|---|---|---|---|---|---|
| CTTATTAATA | ATAAATAAAG | CACATCACTT | GTGTGTGTTC | TGAAAAGCCC | GGGGATCCGT | 1740 |
| CGACCTGCAG | CCAAGCTTGG | CTGTTTTGGC | GGATGAGAGA | AGATTTTCAG | CCTGATACAG | 1800 |
| ATTAAATCAG | AACGCAGAAG | CGGTCTGATA | AAACAGAATT | TGCCTGGCGG | CAGTAGCGCG | 1860 |
| GTGGTCCCAC | CTGACCCCAT | GCCGAACTCA | GAAGTGAAAC | GCCGTAGCGC | CGATGGTAGT | 1920 |
| GTGGGGTCTC | CCCATGCGAG | AGTAGGGAAC | TGCCAGGCAT | CAAATAAAAC | GAAAGGCTCA | 1980 |
| GTCGAAAGAC | TGGGCCTTTC | GTTTTATCTG | TTGTTTGTCG | GTGAACGCTC | TCCTGAGTAG | 2040 |
| GACAAATCCG | CCGGGAGCGG | ATTTGAACGT | TGCGAAGCAA | CGGCCCGGAG | GGTGGCGGGC | 2100 |
| AGGACGCCCG | CCATAAACTG | CCAGGCATCA | AATTAAGCAG | AAGGCCATCC | TGACGGATGG | 2160 |
| CCTTTTTGCG | TTTCTACAAA | CTCTTTTGTT | TATTTTCTA | AATACATTCA | AATATGTATC | 2220 |
| CGCTCATGAG | ACAATAACCC | TGATAAATGC | TTCAATAATA | TTGAAAAAGG | AAGAGTATGA | 2280 |
| GTATTCAACA | TTTCCGTGTC | GCCCTTATTC | CCTTTTTTGC | GGCATTTTGC | CTTCCTGTTT | 2340 |
| TTGCTCACCC | AGAAACGCTG | GTGAAAGTAA | AAGATGCTGA | AGATCAGTTG | GGTGCACGAG | 2400 |
| TGGGTTACAT | CGAACTGGAT | CTCAACAGCG | GTAAGATCCT | TGAGAGTTTT | CGCCCCGAAG | 2460 |
| AACGTTTTCC | AATGATGAGC | ACTTTTAAAG | TTCTGCTATG | TGGCGCGGTA | TTATCCCGTG | 2520 |
| TTGACGCCGG | GCAAGAGCAA | CTCGGTCGCC | GCATACACTA | TTCTCAGAAT | GACTTGGTTG | 2580 |
| AGTATTCACC | AGTCACAGAA | AAGCATCTTA | CGGATGGCAT | GACAGTAAGA | GAATTATGCA | 2640 |
| GTGCTGCCAT | AACCATGAGT | GATAACACTG | CGGCCAACTT | ACTTCTGACA | ACGATCGGAG | 2700 |
| GACCGAAGGA | GCTAACCGCT | TTTTTGCACA | ACATGGGGGA | TCATGTAACT | CGCCTTGATC | 2760 |
| GTTGGGAACC | GGAGCTGAAT | GAAGCCATAC | CAAACGACGA | GCGTGACACC | ACGATGCCTG | 2820 |
| TAGCAATGGC | AACAACGTTG | CGCAAACTAT | TAACTGGCGA | ACTACTTACT | CTAGCTTCCC | 2880 |
| GGCAACAATT | AATAGACTGG | ATGGAGGCGG | ATAAAGTTGC | AGGACCACTT | CTGCGCTCGG | 2940 |
| CCCTTCCGGC | TGGCTGGTTT | ATTGCTGATA | AATCTGGAGC | CGGTGAGCGT | GGGTCTCGCG | 3000 |
| GTATCATTGC | AGCACTGGGG | CCAGATGGTA | AGCCCTCCCG | TATCGTAGTT | ATCTACACGA | 3060 |
| CGGGGAGTCA | GGCAACTATG | GATGAACGAA | ATAGACAGAT | CGCTGAGATA | GGTGCCTCAC | 3120 |
| TGATTAAGCA | TTGGTAACTG | TCAGACCAAG | TTTACTCATA | TATACTTTAG | ATTGATTTAA | 3180 |
| AACTTCATTT | TTAATTTAAA | AGGATCTAGG | TGAAGATCCT | TTTTGATAAT | CTCATGACCA | 3240 |
| AAATCCCTTA | ACGTGAGTTT | TCGTTCCACT | GAGCGTCAGA | CCCCGTAGAA | AAGATCAAAG | 3300 |
| GATCTTCTTG | AGATCCTTTT | TTTCTGCGCG | TAATCTGCTG | CTTGCAAACA | AAAAAACCAC | 3360 |
| CGCTACCAGC | GGTGGTTTGT | TTGCCGGATC | AAGAGCTACC | AACTCTTTTT | CCGAAGGTAA | 3420 |
| CTGGCTTCAG | CAGAGCGCAG | ATACCAAATA | CTGTCCTTCT | AGTGTAGCCG | TAGTTAGGCC | 3480 |
| ACCACTTCAA | GAACTCTGTA | GCACCGCCTA | CATACCTCGC | TCTGCTAATC | CTGTTACCAG | 3540 |
| TGGCTGCTGC | CAGTGGCGAT | AAGTCGTGTC | TTACCGGGTT | GGACTCAAGA | CGATAGTTAC | 3600 |
| CGGATAAGGC | GCAGCGGTCG | GGCTGAACGG | GGGGTTCGTG | CACACAGCCC | AGCTTGGAGC | 3660 |
| GAACGACCTA | CACCGAACTG | AGATACCTAC | AGCGTGAGCA | TTGAGAAAGC | GCCACGCTTC | 3720 |
| CCGAAGGGAG | AAAGGCGGAC | AGGTATCCGG | TAAGCGGCAG | GGTCGGAACA | GGAGAGCGCA | 3780 |
| CGAGGGAGCT | TCCAGGGGGA | AACGCCTGGT | ATCTTTATAG | TCCTGTCGGG | TTTCGCCACC | 3840 |
| TCTGACTTGA | GCGTCGATTT | TTGTGATGCT | CGTCAGGGGG | GCGGAGCCTA | TGGAAAAACG | 3900 |
| CCAGCAACGC | GGCCTTTTTA | CGGTTCCTGG | CCTTTTGCTG | GCCTTTTGCT | CACATGTTCT | 3960 |
| TTCCTGCGTT | ATCCCCTGAT | TCTGTGGATA | ACCGTATTAC | CGCCTTTGAG | TGAGCTGATA | 4020 |
| CCGCTCGCCG | CAGCCGAACG | ACCGAGCGCA | GCGAGTCAGT | GAGCGAGGAA | GCGGAAGAGC | 4080 |

| | | | | | |
|---|---|---|---|---|---|
| GCCTGATGCG | GTATTTTCTC | CTTACGCATC | TGTGCGGTAT | TTCACACCGC | ATATGGTGCA | 4140 |
| CTCTCAGTAC | AATCTGCTCT | GATGCCGCAT | AGTTAAGCCA | GTATACACTC | CGCTATCGCT | 4200 |
| ACGTGACTGG | GTCATGGCTG | CGCCCCGACA | CCCGCCAACA | CCCGCTGACG | CGCCCTGACG | 4260 |
| GGCTTGTCTG | CTCCCGGCAT | CCGCTTACAG | ACAAGCTGTG | ACCGTCTCCG | GGAGCTGCAT | 4320 |
| GTGTCAGAGG | TTTTCACCGT | CATCACCGAA | ACGCGCGAGG | CAGCTGCGGT | AAAGCTCATC | 4380 |
| AGCGTGGTCG | TGAAGCGATT | CACAGATGTC | TGCCTGTTCA | TCCGCGTCCA | GCTCGTTGAG | 4440 |
| TTTCTCCAGA | AGCGTTAATG | TCTGGCTTCT | GATAAAGCGG | GCCATGTTAA | GGGCGGTTTT | 4500 |
| TTCCTGTTTG | GTCACTTGAT | GCCTCCGTGT | AAGGGGAAT | TTCTGTTCAT | GGGGGTAATG | 4560 |
| ATACCGATGA | AACGAGAGAG | GATGCTCACG | ATACGGGTTA | CTGATGATGA | ACATGCCCGG | 4620 |
| TTACTGGAAC | GTTGTGAGGG | TAAACAACTG | GCGGTATGGA | TGCGGCGGGA | CCAGAGAAAA | 4680 |
| ATCACTCAGG | GTCAATGCCA | GCGCTTCGTT | AATACAGATG | TAGGTGTTCC | ACAGGGTAGC | 4740 |
| CAGCAGCATC | CTGCGATGCA | GATCCGGAAC | ATAATGGTGC | AGGGCGCTGA | CTTCCGCGTT | 4800 |
| TCCAGACTTT | ACGAAACACG | GAAACCGAAG | ACCATTCATG | TTGTTGCTCA | GGTCGCAGAC | 4860 |
| GTTTTGCAGC | AGCAGTCGCT | TCACGTTCGC | TCGCGTATCG | GTGATTCATT | CTGCTAACCA | 4920 |
| GTAAGGCAAC | CCCGCCAGCC | TAGCCGGGTC | CTCAACGACA | GGAGCACGAT | CATGCGCACC | 4980 |
| CGTGGCCAGG | ACCCAACGCT | GCCCGAGATG | CGCCGCGTGC | GGCTGCTGGA | GATGGCGGAC | 5040 |
| GCGATGGATA | TGTTCTGCCA | AGGGTTGGTT | TGCGCATTCA | CAGTTCTCCG | CAAGAATTGA | 5100 |
| TTGGCTCCAA | TTCTTGGAGT | GGTGAATCCG | TTAGCGAGGT | GCCGCCGGCT | TCCATTCAGG | 5160 |
| TCGAGGTGGC | CCGGCTCCAT | GCACCGCGAC | GCAACGCGGG | GAGGCAGACA | AGGTATAGGG | 5220 |
| CGGCGCCTAC | AATCCATGCC | AACCCGTTCC | ATGTGCTCGC | CGAGGCGGCA | TAAATCGCCG | 5280 |
| TGACGATCAG | CGGTCCAGTG | ATCGAAGTTA | GGCTGGTAAG | AGCCGCGAGC | GATCCTTGAA | 5340 |
| GCTGTCCCTG | ATGGTCGTCA | TCTACCTGCC | TGGACAGCAT | GGCCTGCAAC | GCGGGCATCC | 5400 |
| CGATGCCGCC | GGAAGCGAGA | AGAATCATAA | TGGGGAAGGC | CATCCAGCCT | CGCGTCGCGA | 5460 |
| ACGCCAGCAA | GACGTAGCCC | AGCGCGTCGG | CCGCCATGCC | GGCGATAATG | GCCTGCTTCT | 5520 |
| CGCCGAAACG | TTTGGTGGCG | GGACCAGTGA | CGAAGGCTTG | AGCGAGGGCG | TGCAAGATTC | 5580 |
| CGAATACCGC | AAGCGACAGG | CCGATCATCG | TCGCGCTCCA | GCGAAAGCGG | TCCTCGCCGA | 5640 |
| AAATGACCCA | GAGCGCTGCC | GGCACCTGTC | CTACGAGTTG | CATGATAAAG | AAGACAGTCA | 5700 |
| TAAGTGCGGC | GACGATAGTC | ATGCCCGCG | CCCACCGGAA | GGAGCTGACT | GGGTTGAAGG | 5760 |
| CTCTCAAGGG | CATCGGTCGA | CGCTCTCCCT | TATGCGACTC | CTGCATTAGG | AAGCAGCCCA | 5820 |
| GTAGTAGGTT | GAGGCCGTTG | AGCACCGCCG | CCGCAAGGAA | TGGTGCATGC | AAGGAGATGG | 5880 |
| CGCCCAACAG | TCCCCCGGCC | ACGGGGCCTG | CCACCATACC | CACGCCGAAA | CAAGCGCTCA | 5940 |
| TGAGCCCGAA | GTGGCGAGCC | CGATCTTCCC | CATCGGTGAT | GTCGGCGATA | TAGGCGCCAG | 6000 |
| CAACCGCACC | TGTGGCGCCG | GTGATGCCGG | CCACGATGCG | TCCGGCGTAG | AGGATCCGGG | 6060 |
| CTTATCGACT | GCACGGTGCA | CCAATGCTTC | TGGCGTCAGG | CAGCCATCGG | AAGCTGTGGT | 6120 |
| ATGGCTGTGC | AGGTCGTAAA | TCACTGCATA | ATTCGTGTCG | CTCAAGGCGC | ACTCCCGTTC | 6180 |
| TGGATAATGT | TTTTGCGCC | GACATCATAA | CGGTTCTGGC | AAATATTCTG | AAATGAGCTG | 6240 |
| TTGACAATTA | ATCATCGGCT | CGTATAATGT | GTGGAATTGT | GAGCGGATAA | CAATTTCACA | 6300 |
| CAGGAAACAG | AA | | | | | 6312 |

( 2 ) INFORMATION FOR SEQ ID NO:4:

( i ) SEQUENCE CHARACTERISTICS:

(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "SYNTHETIC DNA"

(xi) SEQUENCE DESCRIPTION: SEQ ID NO:4:

AGCTGGAGAG TTGAGGTACC C                    21

(2) INFORMATION FOR SEQ ID NO:5:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "SYNTHETIC DNA"

(xi) SEQUENCE DESCRIPTION: SEQ ID NO:5:

AATCAAGATC GCTGGCGTTC ACTGGTG              27

(2) INFORMATION FOR SEQ ID NO:6:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "SYNTHETIC DNA"

(xi) SEQUENCE DESCRIPTION: SEQ ID NO:6:

TTCGGAGCAA CCCCCGGACG CGATGAGCGC A          31

(2) INFORMATION FOR SEQ ID NO:7:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "SYNTHETIC DNA"

(xi) SEQUENCE DESCRIPTION: SEQ ID NO:7:

CCTAAATGTG TCATGCGAAA A                    21

(2) INFORMATION FOR SEQ ID NO:8:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "SYNTHETIC DNA"

(xi) SEQUENCE DESCRIPTION: SEQ ID NO:8:

GGTTGAGTAT TCACCAGTC                       19